(12) United States Patent
Corso et al.

(10) Patent No.: US 6,318,157 B1
(45) Date of Patent: Nov. 20, 2001

(54) HIGH-THROUGHPUT PARALLEL LIQUID CHROMATOGRAPHY SYSTEM

(75) Inventors: Thomas N. Corso, Lansing; Colleen K. Van Pelt, Ithaca, both of NY (US)

(73) Assignee: Advanced Bioanalytical Services, Inc., Itaca, NY (US)

(*) Notice: Subject to any disclaimer, the term of this patent is extended or adjusted under 35 U.S.C. 154(b) by 0 days.

(21) Appl. No.: 09/553,389

(22) Filed: Apr. 20, 2000

Related U.S. Application Data

(60) Provisional application No. 60/130,761, filed on Apr. 23, 1999.

(51) Int. Cl.[7] ............... G01N 31/08; G01N 33/00; G01N 30/02; B01D 15/08
(52) U.S. Cl. ............... 73/61.52; 73/61.56; 210/659; 210/198.2; 422/70
(58) Field of Search ............... 73/61.52, 61.55, 73/61.56, 61.59, 23.41, 23.35; 210/656, 659, 198.2; 422/70

(56) References Cited

U.S. PATENT DOCUMENTS

| | | | |
|---|---|---|---|
| 3,373,872 | 3/1968 | Hrdina | 210/198 |
| 3,508,880 | 4/1970 | Hrdina . | |
| 3,676,649 | * 7/1972 | Burk | 235/151.3 |
| 3,923,460 | 12/1975 | Parrott et al. | 23/230 |
| 3,926,559 | * 12/1975 | Stevens | 23/230 R |
| 4,003,243 | * 1/1977 | Blu et al. | 73/61.52 |
| 4,271,697 | 6/1981 | Mowery, Jr. et al. | 73/61.52 |
| 4,364,263 | 12/1982 | Sankoorikal et al. | 73/61.52 |

(List continued on next page.)

OTHER PUBLICATIONS

Korfmacher et al., "Demonstration of the Capabilities of a Parallel High Performance Liquid Chromatography Tandem Mass Spectrometry System for Use in the Analysis of Drug Discovery Plasma Samples", 1999, pp. 1991–1998.

de Biasi et al., "High Throughput Liquid Chromatography/ Mass Spectrometric Analyses Using a Novel Multiplexed Electrospray Interface", 1999, pp. 1165–1168.

Zeng et al., "Developments of a Fully Automated Parallel HPLC/Mass Spectrometry System for the Analytical Characterization and Preparative Purification of Combinatorial Libraries", Oct. 15, 1998, pp. 4380–4388.

Primary Examiner—Daniel S. Larkin
Assistant Examiner—David J. Wiggins
(74) Attorney, Agent, or Firm—Nixon Peabody LLP; Michael L. Goldman; Daniel W. Sixbey

(57) ABSTRACT

A high-throughput liquid chromatography system capable of parallel separations for increased sample throughput is described. The system comprises valves allowing for the use of multiple liquid chromatography columns and a single injector and pumping system while also minimizing extraneous plumbing and hardware. The system is capable of injecting individual samples and directing them to one of a multiplicity of columns followed by selective output to a detector. The system described allows for up to 16 columns, but the number may vary according to the application. The system may be run in an isocratic or gradient mode. Whereas currently available multi-probe systems incorporate a separate injector for each column, the invention described here uses only one injector and is independent of column number. This removes injector variability along with reducing the amount of pluming and mechanical parts in the system allowing for better separations while providing a more robust system. This device may be interfaced to existing HPLC injector, pumping, and detector technology.

10 Claims, 4 Drawing Sheets

U.S. PATENT DOCUMENTS

| | | | |
|---|---|---|---|
| 4,446,105 | | 5/1984 | Dinsmore et al. ............... 422/70 |
| 4,577,492 | | 3/1986 | Holba et al. . |
| 4,699,718 | | 10/1987 | Jones et al. ............... 210/659 |
| 4,751,185 | | 6/1988 | Ono et al. ............... 436/24 |
| 4,859,342 | | 8/1989 | Shirasawa et al. ............... 210/656 |
| 4,952,126 | * | 8/1990 | Hanaoka et al. ............... 422/70 |
| 5,071,547 | * | 12/1991 | Cazer et al. ............... 210/198.2 |
| 5,093,267 | * | 3/1992 | Miwri et al. ............... 436/93 |
| 5,135,718 | * | 8/1992 | Kawaguchi et al. ............... 422/70 |
| 5,234,586 | | 8/1993 | Afeyan et al. ............... 210/198.2 |
| 5,419,208 | | 5/1995 | Schick ............... 73/863.73 |
| 5,630,943 | | 5/1997 | Grill ............... 210/659 |
| 5,645,728 | | 7/1997 | Hocking et al. ............... 210/656 |
| 5,983,703 | * | 11/1999 | Wylie et al. ............... 73/23.42 |
| 6,175,409 | * | 1/2001 | Nielsen et al. ............... 356/337 |

* cited by examiner

Conventional Chromatogram

Real Time (min)

Column 1

Column 2

Column 3

Column 4

HIGH-THROUGHPUT PARALLEL LIQUID CHROMATOGRAPHY SYSTEM

This application is a continuation-in-part application of serial No. 60/130,761 filed Apr. 23, 1999.

BACKGROUND OF THE INVENTION

High performance liquid chromatography (HPLC) is a versatile technique that allows for separation of compounds with molecular weights ranging from approximately 54 to greater than 450,000 for analysis and/or identification. Detection limits are dependent on the type of detector and may range from femtograms to micrograms at the analytical scale, to milligrams at the semipreparative scale, and to grams at the preparative scale. The technique is relatively robust having no requirements for volatile compounds or derivatives and allows for the analysis of thermally labile compounds. Samples with wide ranging polarities can be analyzed in a single analysis. HPLC provides relatively fast analysis times, reproducibility, and sensitivity. Typical run times (analysis time) range from 5 to 30 minutes but can be longer than an hour for gradient runs. Run times under a minute have been achieved on microbore columns, but more often than not, these fast separations have limited applications because less than optimal chromatographic separations are achieved.

High performance liquid chromatography coupled with mass spectrometry (MS) is common for quantitative analysis, confirmation of identity, and structural determination of unknowns. Relatively recent developments in mass spectrometry, especially, electrospray ionization (ESI) and atmospheric pressure ionization (API), have made the coupling a useful and reliable means for routine liquid chromatography/mass spectrometers (LC/MS) sample analysis. Specifically, tandem MS (LC/MS/MS) provides very high selectivity and specificity and as a result has become a powerful tool for pharmaceutical analyses and quantization. Although LC coupled with MS/MS has become an indispensable tool for pharmacological analysis by providing high sensitivity along with relatively fast analysis times, there still is an increased demand for higher sample throughput than is provided today. Currently, an analytical bottleneck exists.

In addition, drug discovery processes have been greatly accelerated by advances in combinatorial chemistry. The analytical demands created by modern drug discovery practices require improved sample preparation and analysis capabilities. Combinatorial chemical syntheses are performed in parallel whereas LC analyses used to characterize the products of parallel syntheses are currently performed in a serial fashion thus creating an analytical bottleneck. Because of the need for high sample throughput, chromatographic separations are often sacrificed in order to decrease analysis times. Although faster analyses are achieved, often it leads to compromised chromatographic separation resulting in lower accuracy and precision.

The major disadvantage of serial LC analysis is the inherent "idle time" that occurs during pre- and post-analyte elution. Here, idle time refers to the time during the analytical run that the analyte is not being detected; for example, injection time and preparation, elution time of non-analyte eluting peaks, column wash cycles, and column equilibration. Typically in an HPLC run, the analytes of interest elute in a short time relative to the total run time of the analytical run. To date, the most common approach taken is to reduce chromatography separation times as a means of increasing sample throughput. This approach will inherently be limited because it is conducted in a serial fashion whereas the syntheses are conducted in a parallel fashion.

U.S. Pat. No. 4,364,263 to Sankoorkal et al discloses a high pressure liquid chromatographic system including a plurality of parallel columns with a valving system which directs one solvent/sample flow to a single column and then to a detector.

U.S. Pat. No. 3,373,872 to Hodina discloses a chromatography apparatus where a two way valve selectively connects one of two columns to a solution pump.

Several different approaches have been taken to achieve parallel chromatography and in order to increase throughput. de Biasi et al. proposed a four-channel multiplexed electrospray interface used in combination with four LC columns and multi-syringe probe injector, such as a Gilson Multiprobe. This interface rapidly switches between multiple liquid streams which results in lower dwell times and reduced sensitivity. [de Biasi et al., *Rapid Communication In Mass Spectrometry*, 1999, Vol. 13, pgs. 1165–1168] The approach may be useful for unknowns where sensitivity is not an issue, but would it be useful for PK analysis where sensitivity is of great importance. Also, this approach uses a specific multiprobe injector system that contains multiple injectors with many valves and mechanical parts. Additionally, because this approach requires modifications to the mass spectrometer ion source, the user is limited to a specific instrument vendor.

Another approach was taken by Korfmacher et al. who used two separate LC pumping systems, two autosamplers, and two columns connected via a divert valve to a single mass spectrometer. A major disadvantages of this system is that it requires a significant investment in capital equipment as it contains the HPLC hardware of two conventional systems. [Korfacher, 1999]

Zeng et al. [*Analytical Chemistry*, 1998, Vol. 70, pgs. 4380–4388] have shown parallel separations using two columns and an autosampler equipped with multiple injectors (multiprobe) for automated characterization of and purification of combinatorial libraries. This system operates two analytical or preparative columns in parallel through a valving system and dual electrospray ionization interface. The design of this dual interface permits the ionization of the analytes in one line to impact the ionization of the analytes in the other, and an additional disadvantage of this system is that two isobaric analytes cannot be quantified simultaneously. This injector system employed contains eight separate injectors each with a corresponding sample probe (the authors used two for this work). The system was configured so that the autosampler's two injectors simultaneously admitted the samples into two different corresponding columns and then to a dual sprayer ionspray interface followed by introduction into a single mass spectrometer. The authors system works for qualitative applications where molecular weights are known prior to analyses while also having a requirement of varying m/z values in the analyses. However, for instances where same transition m/z value is desired for many samples, such as the case for quantitative analyses, MS can only measure one ion beam at a time on current instrumentation. There are several disadvantages to the system described above: 1. The high numbers of mechanical parts (i.e. valves and injector probes) increase the rate of mechanical failure. 2. The additional tubing lengths needed to connect the numerous valves contribute to increased dead volume and swept volume and resulting in decreased chromatographic resolution. 3. Because separate probes (injector needles and syringe barrels) inject samples into separate valves, each with separately plumbed lines, greater variability results to that of a single injector system (fewer parts). 4. The inherent cost of the system is increased because of the increased hardware and complexity of the system. In addition, a user is limited to this particular manufacturer and specific system.

SUMMARY OF THE INVENTION

It is a primary object of the present invention to provide a novel and improved high-throughput parallel liquid chromatography system and method utilizing "staggered" parallel chromatography in order to admit analytes sequentially from a multiplicity of columns into a detector.

Another object of the present invention is to provide a novel and improved high-throughput parallel liquid chromatography system using a single injector and a plurality of parallel columns to admit analytes to a single detector. A significant increase in analysis speed is achieved because analytes eluding from a given column are directed to the detector only during elution times.

Yet another object of the present invention is to provide a novel and improved high-throughput parallel liquid chromatography system which removes idle time, i.e. the time during the separation that peaks are not eluting.

Still another object of the present invention is to provide a novel and improved high-throughput parallel liquid chromatography system which allows for the choice of various vendor autosamples, LC pumps, ion sources, and mass spectrometers to be used. Existing technology can be coupled with the system and there are benefits with this flexibility as certain analyses work better with specific hardware (i.e. autosamplers, LC pumps, ion sources, and mass spectrometers).

A further object of the present invention is to provide a novel and improved high-throughput parallel liquid chromatography system using only three control valves which is less expensive than other known systems which require many valves and mechanical parts. This reduces the chance of mechanical failure, and three valves can be used with from two to eight chromatography columns.

Yet a further object of the present invention is to provide a novel and improved high-throughput parallel liquid chromatography system wherein solvent from a pumping unit is divided into a plurality of streams equal in number to plurality of parallel columns. The streams are sequentially provided to a single injector which introduces samples to the solvent stream selected for passage to the injector. A group of multiposition valves operate to a pass a selected stream to the injector, to one of the plurality of columns and from the column to a detector. The same valves cause the remaining streams to bypass the injector, to pass individually to other columns in the plurality of columns and to then pass to a waste conduit or container.

A still further object of the present invention is to provide a novel and improved high-throughput parallel liquid chromatography system composed of a single LC pumping system, autosampler, and mass spectrometer used in combination with plural columns, in a parallel configuration, and a valving system. The valving system is composed of three valves. Two of the valves work in unison to select which of the columns receives the injection while simultaneously providing mobile phase to all columns. The third valve simply selects which column is to be in-line with the mass spectrometer, while the effluent from the other three are directed to a waste container. This parallel chromatography system can easily be modified to perform gradient LC. Gains in throughput depend on the assay, but typically range from 2–4× to that of conventional LC method of analysis. For longer run times even high throughput may be achieved. The valves could be designed incorporate from 2–8 columns.

These and other objects of the present invention are achieved by providing a high-throughput parallel liquid chromatography system connectable to a detector. This system includes a plurality of parallel columns which are to receive separate streams of liquid, one of which will be provided to the detector at any given time. The system further includes at least one pump for pumping a carrier fluid to the system and the fluid from the pump is divided into a plurality of separate streams equal in number to the number of columns intended to receive streams of liquid. A first multipurpose valve having a number of input ports at least equal to number of separate streams from the pump receives a stream at each of said input ports. This first multipurpose valve has a plurality of output ports at least equal in number to the number of separate streams plus at least one additional outlet port connected to the injector. The outlet ports of the first multiposition valve, with the exception of the outlet port connected to the injector, are directly connected to an equal number of inlet ports in a second multiposition valve. The injector outlet is connected directly to an additional inlet port in the second multiposition valve. The second multiposition valve has a plurality of output ports at least equal in number to the number of streams provided to the first multiposition valve, and each of these second multiposition outlet ports is connected to the inlet of one of the parallel columns. One column receives the stream which has passed through the injector which contains a sample while remaining columns receive carrier streams without a sample. The output streams from the columns pass to a third multiposition valve which directs the stream with the sample to a detector and the remaining streams to waste. The three multiposition valves are sequentially switched to direct a new carrier stream to the injector, to a different column and then to the detector.

DETAILED DESCRIPTION OF THE INVENTION

In most conventional chromatograms the peak elution time is only a small percentage of the total run time, as there is a significant amount of "wasted" time before the compound of interest elutes, as well as during the re-equilibration period of the column. The general idea behind the present approach to parallel chromatography is to use this wasted time by staggering injections onto separate columns in such a way that the chromatographic window of interest is always eluting from one of the columns. The effluent from the particular column that has the compound of interest eluting, is diverted to the mass spectrometer. An increase in sample throughput is achieved by staggering injections onto the plural columns, allowing the mass spectrometer to always be analyzing the chromatographic window of interest. Using this approach, the true optimized run time is the sum of the widths of the desired peaks. This parallel chromatography unit can operate under both gradient and isocratic LC conditions. To demonstrate the utility of the system, six test compounds were analyzed using gradient chromatography conditions. The results from a pre-study assay evaluation (PSAE) tray of standards and quality control (QC) samples from extracted spiked human plasma are presented. The correlation coefficients (r) of all six compounds were greater than 0.99 and the relative standard deviation of the QC samples did not exceed 8.1%, which is well within the acceptance criteria of the pharmaceutical industry for LCMS. For this particular analysis the parallel chromatography system decreased the overall runtime from 4.5 min to 1.65 min and therefore increased the overall throughput by a factor of 2.7 in comparison to conventional means of analyses.

Figure 1:
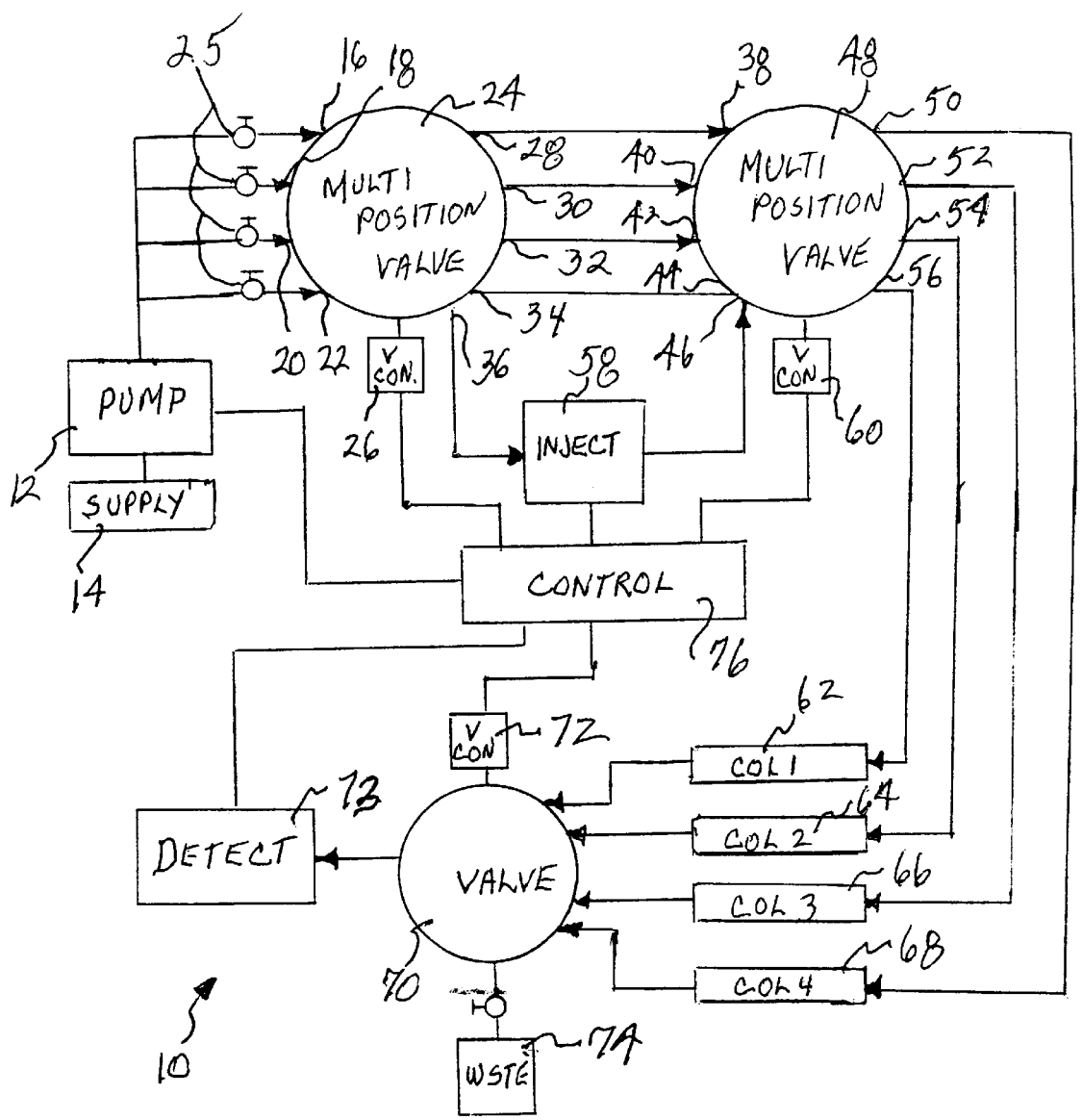
FIG. 1 is a block diagram of the high throughput parallel liquid chromatography system of the present invention.

With reference to FIG. 1, the high-throughput parallel liquid chromatography system of the present invention indicated generally at 10 is uniquely designed to admit analytes sequentially from a multiplicity of columns into a detector. For purposes of illustration, the chromatography system will be described as a four column system, but any plurality of parallel columns from two up to eight columns may be employed if valves with a sufficient number of ports are incorporated in the system.

For isocratic liquid chromatography conditions, only one pump 12 is required to provide four solvent streams from a source 14 over separate input lines to the input ports 16, 18, 20 and 22 of a multiposition valve 24. Pressure control valves 25 in each input line balance the flow of the various streams. The multiposition valve 24 includes a valve actuator or controller 26 which causes the multiposition valve 24 to selectively switch three of the solvent streams from the valve input ports to three of four valve output ports 28, 30, 32, and 34 and the fourth solvent stream to a fifth valve outlet port 36. Thus the stream which would normally flow through one of the outlet ports 28, 30, 32 or 34 is diverted to the outlet port 36, while the remaining three streams pass directly to three of five valve input ports 38, 40, 42, 44 and 46 for a second multiposition valve 48. This second multiposition valve has four valve outlet ports 50, 52, 54 and 56.

The outlet port 36 of the multiposition valve 24 is connected to direct a carrier or solvent stream to an injector 58 (autosampler), which introduces a sample into the solvent stream, and the stream exiting the injector is directed to the valve inlet port 46 for the second multiposition valve 48. A valve actuator or controller 60 for the second multiposition valve causes this valve to direct the streams which have bypassed the injector 58 to three of the four valve outlet ports 50, 52, 54 and 56 and the stream from the inlet port 46 to the remaining valve outlet port. Each of the valve outlet ports for the second multiposition valve is connected to one of four chromatography columns 62, 64, 66 and 68, and the output streams from these columns are separately directed to a post-column diverter valve 70. A valve actuator or controller 72 for the diverter valve causes this valve to select the stream which had previously passed through the injector 58 from the column output streams and to pass this stream to a detector 73 (i.e. mass spectrometer) while diverting the remaining column output streams to a waste line 74. The diverter valve 70 can be structured the same as the valves 24 and 48 with one output port connectible to the detector 73 and the remaining output ports connectible separately to the waste line 74. Ideally, as shown in FIG. 2, the diverter valve provides a single outlet to the waste line for all streams being diverted to waste.

The various components of the parallel chromatography system need to be integrated in such a way as to act as one integrated system. This can be accomplished through contact closures, TTL logic, or RS232. These signal(s) are sent to the electric actuators that control the valve positions. The control signals may be sent by a desired device, for example an autosampler, LC pump, LC pump controller, mass spectrometer, or custom software. Thus a suitable controller 76 is connected to control the valve actuators 26, 60 and 72 and may be responsive to signals from the pump, the injector and the detector. The controller can time the period between injections to successive columns in accordance with the time required to acquire the appropriate chromatographic information by the detector for each column.

The multiposition valve 24 selects an input stream and sends it to the injector, while the second multiposition valve insures that the selected stream passes to its corresponding chromatography column. The diverter valve then directs the selected stream to the detector 72. At the desired timing intervals the valves 24, 48 and 70 are activated to divert a new stream to the detector 72, and this process is repeated for each of the streams at the appropriate time intervals.

Figure 2:
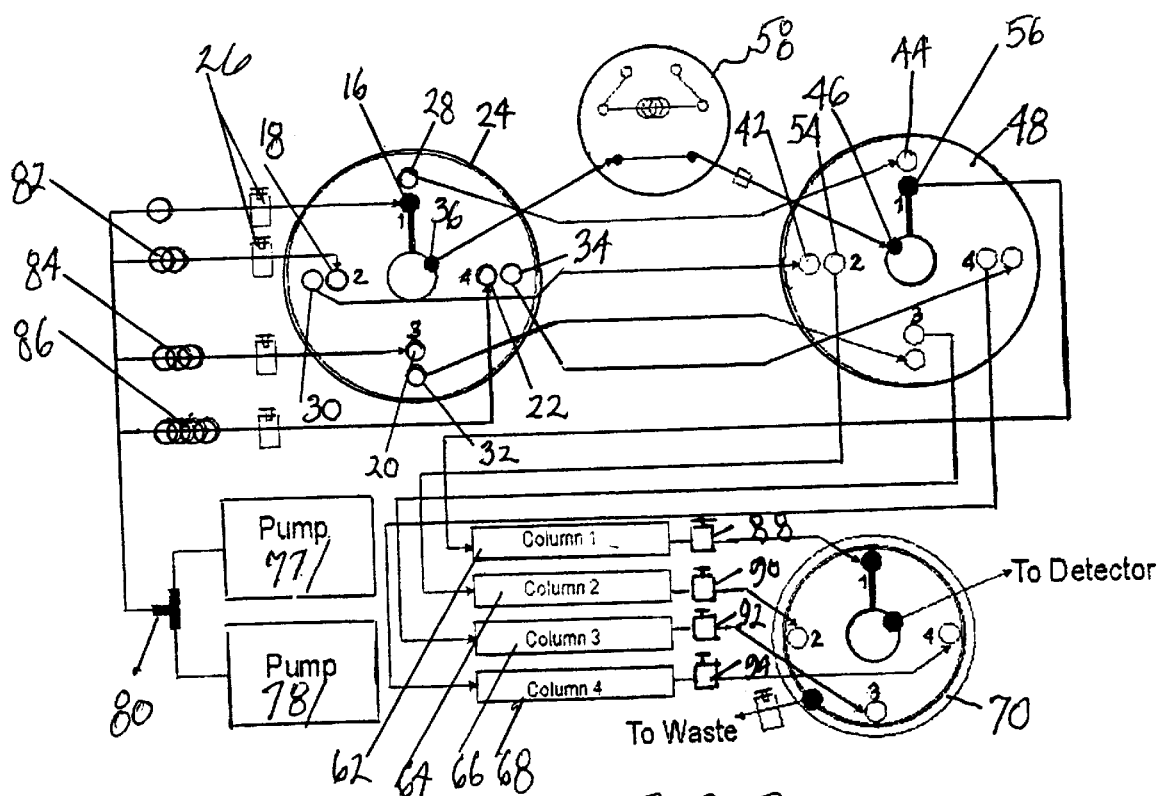
FIG. 2 is a flow schematic of a second embodiment of the high throughput parallel liquid chromatography system of the present invention.

The valve diagrams of FIG. 2 will provide a better understanding of the valve operation for the high-throughput parallel liquid chromatography system 10. The multiposition valve 24 is set to divert stream 1 which passes in through valve input port 16 from output port 28 to outlet port 36, the injector 58 and to input port 46 for the secondary multiposition valve 48. This secondary multiposition valve is set to direct stream 1 to column 62, and post-column diverter valve 70 is positioned to direct stream 1 to the detector 72. Streams 2, 3 and 4 at the valve input ports 18, 20 and 22 are caused to bypass the injector and pass through the second multiposition valve to the columns 64, 66 and 68. These three streams are then directed to waste by the post-column diverter valve 70. When the time required to acquire the chromatographic information from stream 1 has elapsed, the valves 24, 48 and 70 are activated to the stream 2 position shown in FIG. 2. Now stream 2 through the valve input port 18 is directed through the injector and into the second multiposition valve 48 through the inlet port 46. Now, however, the valve 48 sends this selected stream 2 through the valve outlet port 54 to column 64. The post-column diverter valve 70 has also moved to the stream 2 position to divert the stream from column 64 to the detector.

In FIG. 2, two pumps 77 and 78 are used for the high-throughput parallel liquid chromatography system 10 to provide solvent to a mixing tee 80. For gradient liquid chromatography conditions tubing of various lengths is placed in-line after the mixing tee in order to time the arrival of the four solvent streams to the injector at predetermined time intervals. The time intervals between stream arrivals are determined by the time required to acquire the appropriate chromatographic information by the mass spectrometer. Therefore, the volume of delay loop 82 is equal to the flow rate of the LC effluent times the mass spectrometer acquisition window. The volume of delay loop 84 is twice the volume of delay loop 82 and the volume of delay loop 86 is 3 times the volume of delay loop 82. Alternatively, valves containing multiple predetermined tubing lengths (volumes) may be added for more convenient method development. For isocratic conditions no delay loops are necessary.

Considering the system of FIG. 2 in greater detail, the system includes two binary Shimadzu LC-10A pumps and a Shimadzu SCL-10A pump controller (Shimadzu, Inc., Columbia, Md.). Solvent A through pump 77 was 0.1% acetic acid in water, and solvent B through pump 78 was acetonitrile. The LC gradient began at 20% solvent B, and was then ramped over a 0.1 min interval to reach 70% at 0.5 min. Solvent B was held at 70% until 2.5 min, when it was decreased back to the original 20%. The gradient program ended at 6.57 min. The total flow rate from the pumping system was 748 $\mu$L/min, which was split equally four ways via the mobile phase splitter 80 (Valco Instrument Co. Inc., Houston, Tex.) shown in FIG. 2. The mobile phase then entered various lengths of 0.020 in. PEEK tubing. The length of this mobile phase delay tubing was dependent on the amount of time the gradient needed to be delayed in each particular line before reaching the head of the column. In this study, line 1 had a delay tubing length of 12 in., line 2 had 5 ft, line 3 had 10 ft, and line 4 had 15 ft. Valve 24 and valve 48 were constructed by Valco Instrument Co. Inc. (Houston, Tex.). The valves were rotated concurrently and were always in the same relative position in order to select which of the four lines and therefore which column would be in-line with the autosampler 58 while continuously providing mobile phase to all four lines. This valve design allows for a given stream to receive an injection of sample, while maintaining the flow, and thus allowing for separation to occur, in the other unselected lines. The autosampler 58 was a Perkin Elmer Series 200 autosampler (Perkin Elmer Corp., Norwalk, Conn.) and the injection volume was 20 $\mu$L. The autosampler injected every 1.65 min.

Four identical Genesis, $C_{18}$, 4 $\mu$m, 2.1.1 mm×50 mm (Jones Chromatography USA Inc., Lakewood, Colo.) LC columns 62, 64, 66 and 68 manufactured in the same lot were positioned following valve 48 in the flow path shown in FIG. 2. Located after each of the columns was an adjustable PEEK tee 88, 90, 92 and 94 (Upchurch Scientific, Oak Harbor, Wash.). Two ends of each tee were occupied by the inlet and the outlet of the flow and the third opening of the tee was occupied with a PEEK screw. This screw could be adjusted to equilibrate the back pressures of the effluent corresponding to each of the four lines. Typical back pressure for each of the lines was 445 psi. It should be noted that high pressure tees or other pressure regulating devices could be placed prior to the columns to decrease the total system dead volume in future parallel chromatography systems. Following the back pressure adjustment tees in FIG. 2 is valve 70 also constructed by Valco Instrument Co. Inc. (Houston, Tex.). This third valve acts completely independent of valve 24 and valve 48. Valve 70 diverts the effluent from the particular line with the chromatographic window of interest eluting to the detector while directing the effluent form the other three lines to waste.

The mass spectrometer instrument 72 used was a Micromass Quattro II (Cheshire, UK) equipped with a z-spray source and operated in the positive ion electrospray ionization mode. The z-spray desolation temperature and capillary voltage were 390° C. and 3500 V, respectively. The collision energy used was 15 V and the dwell time for each transition was 50 msec.

Figure 3:
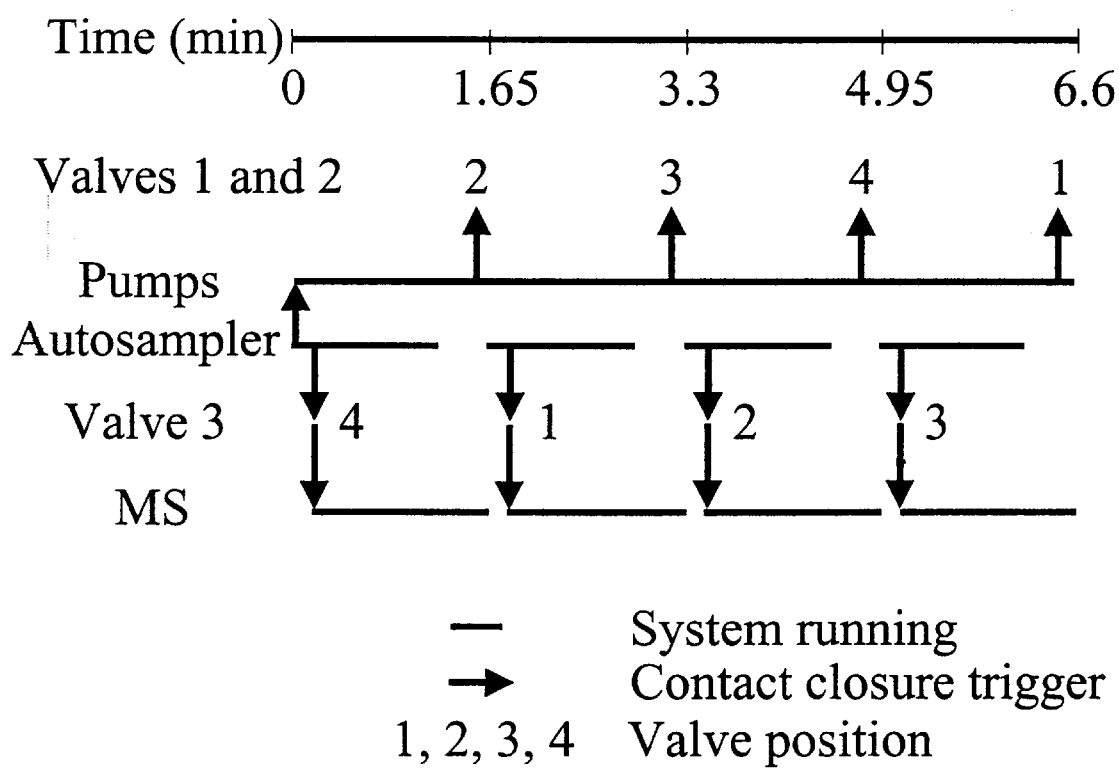
FIG. 3 is a schematic showing the events and event timing for a single parallel chromatography cycle using the high-throughput parallel liquid chromatography system of the present invention.

The various components of the parallel chromatography system 10 need to be integrated in such a way as to act as one cohesive system. This has been accomplished through contact closures where valve switching normally occurs at sequential times required to obtain known peak widths. FIG. 3 shows the triggered events in a single parallel chromatography cycle. To initiate the first cycle in a run containing many cycles, the autosampler is manually started. Then, as shown in FIG. 3, at 0.01 min, the autosampler by control 76 triggers the pumps 77 and 78 to begin their 6.57 min gradient program. At 0.20 min the autosampler by control 76 simultaneously turns valve 70 (valve 3) and starts a 1.53 min long MS run. Then, prior to the autosampler making its second injection, valve 24 (valve 1) and valve 48 (valve 2) are signaled to turn by a contact closure provided to control 76 by the pumps, while valve 70 (valve 3) holds position for a short time longer than that required for the known peak width. The autosampler injects every 1.65 min for a total of four times in a single chromatography cycle. As many of these cycles as necessary are repeated depending on the number of samples. The above explains how in this particular analysis the signaling mechanism was ultimately controlled by the autosampler, but depending on the system, the relays could also be directed from the pumps, the mass spectrometer, or custom software.

Figure 4:
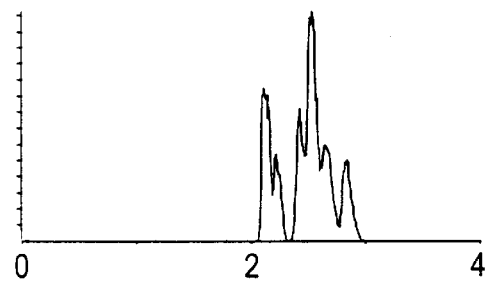
FIG. 4 shows a TIC chromatogram of a conventional analysis of six test compounds.
Figure 5:
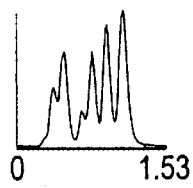
FIG. 5 shows TIC mass spectrometer files for each of the four columns of the high-throughput parallel liquid chromatography system of the present invention relative to their elution times.
Figure 5:
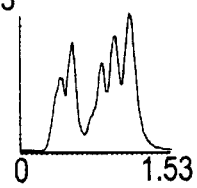
Figure 5:
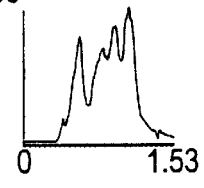
Figure 5:
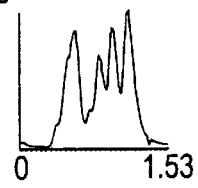

FIG. 4 shows the conventional anaylsis of the six test compounds. The total time between injections was 4.5 min although all of the analytes eluted in a 1 minute interval. Therefore the majority of the run time in this analysis was spent either waiting for the compounds to elute or waiting for the column to re-equilibrate to the initial conditions. This scenario is common for conventional LC analyses. Consequently, the ability to utilize the intervals in a chromatogram before and after the compounds of interest elute, would significantly enhance sample throughput. The objective of the parallel chromatography system presented here is to make use of this idle analysis time by staggering injections onto different columns in timed intervals, allowing the mass spectrometer to always be analyzing the chromatographic window of interest. This is pictorially explained in FIG. 5, which show the elution of the chromatographic window for each of the four columns in a single chromatography cycle.

What is claimed is:

1. A high-throughput parallel liquid chromatography system connectable to a detector, the system comprising:

at least one pump for introducing a carrier into the system;

at least two parallel columns;

an actuatable, multipositional first valve having a plurality of ports with each port thereof in fluid communication with the at least one pump and with each port being dedicated to one of the at least two columns;

an actuatable, multipositional second valve having a plurality of ports with each port thereof being dedicated to and in fluid communication with one of the at least two columns and the like dedicated port of the first valve;

an actuatable, multipositional diverter valve operably connectable to the detector and having a plurality of ports with each port thereof being dedicated to and in fluid communication with one of the at least two columns and the like dedicated ports of the first and second valves; and an injector disposed in selectable fluid communication between the respective ports of first and second valves for introducing samples to the carrier, whereby upon selection of one of the at least two columns, the first, second, and diverter valves actuated to position the respective dedicated ports in fluid communication with one another through the injector so that the sample received by the injector is deliverable to the detector.

2. The high-throughput parallel liquid chromatography system according to claim 1, wherein the carrier is introduced to the ports of the first valve from the at least one pump at varying time intervals.

3. A high-throughput parallel liquid chromatography system connectable to a detector comprising:

at least one pump for introducing a liquid carrier into the system, at least first and second parallel columns each having an inlet and an outlet, a multiposition first valve having at least first and second inlet ports, a fluid conduit connected between said pump and the at least first and second inlet ports of said multiposition first valve and formed to divide the liquid carrier from said pump into at least first and second carrier streams and to provide the first carrier stream to the first inlet port of said multiposition first valve and the second carrier stream to the second inlet port of said multiposition first valve, said multiposition first valve having an injector outlet port and at least first and second outlet ports to normally receive the first and second carrier streams respectively from said first and second input ports, said at least first and second outlet ports of said multiposition first valve being connected to at least first and second inlet ports for a second multiposition valve, said second multiposition valve having an injector inlet port and at least first and second outlet ports to normally receive first and second carrier streams from the first and second inlet ports for said second multiposition valve, an injector for injecting a sample into a carrier stream connected between the injector outlet port of said multiposition first valve and the injector inlet port of said multiposition second valve, the first outlet port of the at least two outlet ports for said multiposition second valve being connected to the inlet of said first parallel column and the second outlet port of the at least two outlet ports for said multiposition second valve being connected to the inlet of said second parallel column, the outlets of said at least first and second parallel columns being connected to a multiposition third valve, said multiposition third valve having at least first and second input ports and a first and second output port, the first input port and second input port of the at least two input ports for said multiposition third valve being connected to said first and second outlets respectively of said at least first and second parallel columns, the first output port of said multiposition third valve being connected to said detector and the second output port of said multiposition third valve being connected to a waste receiver.

4. The high-throughput parallel liquid chromatography system of claim 3 wherein said fluid conduit connected between said pump and the at least first and second inlet ports of said multiposition first valve includes a delay unit to delay the provision of said second carrier stream to said second inlet port of said multiposition first valve relative to the time that said first carrier stream is provided by said fluid conduit to the first inlet port of said multiposition first valve.

5. The high-throughput parallel liquid chromatography system of claim 3 which includes a valve control unit to control the operation of said first, second and third multiposition valves, said valve control unit operating during a first chromatographic period to cause said multiposition first valve to divert said first liquid carrier stream from the first outlet port thereof to the injector outlet port, to cause said multiposition second valve to direct the carrier stream from the injector inlet port thereof to the first outlet port for said multiposition second valve and to cause said multiposition third valve to direct a stream from the first input port of said multiposition third valve to the first output port thereof, said multiposition third valve operating to connect all remaining input ports of the at least first and second input ports thereof to the second output port thereof.

6. The high-throughput parallel liquid chromatography system of claim 5 wherein said valve control unit operates during a second chromatographic period subsequent to said first chromatographic period to cause said multiposition first valve to divert said second liquid carrier stream from the second outlet port thereof to the injector outlet port, to cause said multiposition second valve to direct the carrier stream from the injector inlet port thereof to the second outlet port for said multiposition second valve and to cause said multiposition third valve to direct a stream from the second input port of said multiposition third valve to the first output port thereof, said multiposition third valve operating to connect all remaining input ports of the at least first and second input ports thereof to the second output port thereof.

7. The high-throughput parallel liquid chromatography system of claim 6 wherein said fluid conduit connected between said pump and the at least first and second inlet ports of said multiposition first valve includes a delay unit to delay the provision of said second carrier stream to said second inlet port of said multiposition first valve relative to the time that said first carrier stream is provided by said fluid conduit to the first inlet port of said multiposition first valve.

8. A method for liquid chromatography which includes:

providing a plurality of liquid carrier streams for an equal number of parallel columns, each column having an input and an output, directing each carrier stream to the input of a separate column for receiving said carrier stream, injecting a sample into a selected first of said carrier streams prior to said selected first carrier stream reaching the input of a first column, directing the output of the first column receiving the selected first sample bearing carrier stream to a chromatographic detector, directing the outputs of the remaining columns to a waste receiver, operating after a time to acquire chromatographic information from the selected first sample bearing carrier stream has elapsed to inject a sample into a selected second carrier stream prior to the input of a second column for receiving said second carrier stream, directing output material from the output of said second column to the chromatographic detector, and directing output material from the remaining columns to a waste receiver.

9. The method of claim 8 which includes selecting each carrier stream after the first and second carrier streams in succession to receive a sample.

10. The method of claim 9 which includes delaying the provision of each carrier stream relative to the next preceding carrier stream to the input of the column for receiving said carrier stream.

* * * * *